United States Patent [19]

Combs et al.

[11] Patent Number: 5,562,708
[45] Date of Patent: Oct. 8, 1996

[54] METHOD AND APPARATUS FOR TREATMENT OF ATRIAL FIBRILLATION

[75] Inventors: William J. Combs, Eden Prairie; Edwin G. Duffin, New Brighton; T. V. Rao, Coon Rapids, all of Minn.

[73] Assignee: Medtronic, Inc., Minn.

[21] Appl. No.: 230,577

[22] Filed: Apr. 21, 1994

[51] Int. Cl.⁶ .................................................. A61N 1/39
[52] U.S. Cl. .............................. 607/4; 607/148; 607/129; 607/14
[58] Field of Search .................. 607/14, 148, 4, 607/5, 9, 129

[56] References Cited

U.S. PATENT DOCUMENTS

| | | | |
|---|---|---|---|
| Re. 27,757 | 9/1973 | Mirowski | 128/419 D |
| 3,937,226 | 2/1976 | Funke | 128/419 D |
| 4,088,140 | 5/1978 | Rockland et al. | 607/14 |
| 4,266,551 | 5/1981 | Stein | 128/419 PG |
| 4,275,737 | 6/1981 | Thompson et al. | 128/419 PG |
| 4,340,062 | 7/1982 | Thompson et al. | 128/419 PG |
| 4,406,286 | 9/1983 | Stein | 128/419 PG |
| 4,407,288 | 10/1983 | Langer et al. | 128/419 PG |
| 4,548,209 | 10/1985 | Wielders et al. | 128/419 D |
| 4,554,922 | 11/1985 | Prystowsky et al. | 607/14 |
| 4,595,009 | 6/1986 | Leinders | 128/419 D |
| 4,649,931 | 3/1987 | Beck | 128/708 |
| 4,693,253 | 9/1987 | Adams | 128/419 D |
| 4,800,883 | 1/1989 | Winstrom | 128/419 D |
| 4,821,723 | 4/1989 | Baker, Jr. et al. | 128/419 D |
| 4,830,006 | 5/1989 | Haluska et al. | 128/419 PG |
| 4,880,005 | 11/1989 | Pless et al. | 128/419 PG |
| 4,953,551 | 9/1990 | Mehra et al. | 128/419 D |
| 4,958,632 | 9/1990 | Duggan | 128/419 PG |
| 4,971,070 | 11/1990 | Holleman et al. | 128/784 |
| 5,022,395 | 6/1991 | Russie | 128/419 PG |
| 5,161,528 | 11/1992 | Sweeney . | |
| 5,163,427 | 11/1992 | Keimel | 128/419 D |
| 5,239,999 | 8/1993 | Imran | 128/642 |
| 5,243,978 | 9/1993 | Duffin, Jr. | 607/11 |
| 5,269,298 | 12/1993 | Adams . | |
| 5,282,836 | 2/1994 | Kreyenhagen . | |
| 5,403,356 | 4/1995 | Hill et al. | 607/14 |

FOREIGN PATENT DOCUMENTS

| | | |
|---|---|---|
| 0060117 | 9/1982 | European Pat. Off. . |
| 0095726 | 12/1983 | European Pat. Off. . |
| 0206248 | 12/1986 | European Pat. Off. . |
| 0347353 | 12/1989 | European Pat. Off. . |
| 0420563 | 4/1991 | European Pat. Off. . |
| 0550344 | 7/1993 | European Pat. Off. . |
| 0574609 | 12/1993 | European Pat. Off. . |
| 0588127 | 3/1994 | European Pat. Off. . |
| 0594269 | 4/1994 | European Pat. Off. . |
| 0594271 | 4/1994 | European Pat. Off. . |
| 2528708 | 12/1983 | France . |
| 9218198 | 10/1992 | WIPO ........................... A61N 1/39 |
| 9306886 | 4/1993 | WIPO . |
| 9309844 | 5/1993 | WIPO . |

OTHER PUBLICATIONS

Allessie et al., "Regional Control of Atrial Fibrillation by Rapid Pacing in Conscious Dogs", *Circulation*, 1991;84:1689–1697.

Arzbaecher, "Automatic Tachycardia Recognition", *Pace*, vol. 7, May–Jun., Part II, 1984, pp. 541–547.

Daubert et al., "Prevention of Atrial Tachyarhythmias Related to Advanced Interatrial block by Permanent Atrial Resynchronization", *Pace*, vol. 14, Apr. 1991, Part II, p. 648.

*Primary Examiner*—William E. Kamm
*Assistant Examiner*—Kennedy J. Schaetzle
*Attorney, Agent, or Firm*—Harold R. Patton; Reed A. Duthler

[57] ABSTRACT

A pacemaker system adapted to deliver pacing pulses in the presence of fibrillation. The pacing pulses are delivered via large surface area electrodes of the type normally used to accomplish defibrillation or cardioversion using high voltage pulses. An extended pulse train is delivered in order to gradually entrain greater portions of heart tissue, until a sufficient percentage of tissue is entrained to interrupt fibrillation. The invention is believed most applicable to treatment of atrial fibrillation.

17 Claims, 6 Drawing Sheets

METHOD AND APPARATUS FOR TREATMENT OF ATRIAL FIBRILLATION

BACKGROUND OF THE INVENTION

This invention relates generally to implantable stimulators and, more specifically, to implantable pacemakers, cardioverters and defibrillators.

Over the years, numerous methods have been proposed for pacing the heart in an attempt to interrupt tachycardias. These include such pacing modalities as overdrive pacing, burst pacing, autodecremental overdrive pacing, and others. These pacing modalities have been formulated to interrupt aberrant reentrant conduction which may lead to sustained tachycardias in one or more chambers of the heart.

It has been proposed that tachycardias could be prevented or interrupted by the use of multi-site cardiac pacing. One early example of multi-site cardiac pacing to terminate or prevent tachyarrhythmia is disclosed in U.S. Pat. No. 3,937,226 issued to Funke. In this device, a number of small surface area pacing electrodes are provided, each coupled to a separate output circuit and amplifier. The disclosed device is equivalent to five or more separate cardiac pacemaker output circuits of conventional design, all adapted to be triggered to pace simultaneously at various locations around the heart. It is hypothesized that by stimulating simultaneously at locations spread around the heart, synchronous with a sensed QRS complex, arrhythmias could be prevented by producing a more nearly simultaneous depolarization of cardiac tissues.

In contrast, fibrillation has generally been treated by means of high energy shocks, which, in the context of implantable anti-arrhythmia devices, are applied by means of large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

In the context of atrial fibrillation, a proposed pacemaker/defibrillator is disclosed in PCT Application No. US92/02829, Publication No. WO 92/18198 by Adams et al, incorporated herein by reference in its entirety. In this reference careful synchronization of the high voltage atrial defibrillation pulse to the ventricles to avoid induction of ventricular tachycardia or fibrillation is discussed. Delivery of an atrial defibrillation pulse at an inappropriate time may induce ventricular arrhythmias, including ventricular fibrillation.

Use of pacing pulses delivered at multiple sites within the atria to prevent the occurrence of atrial tachyarrhythmias including atrial flutter, which may in some cases progress to atrial fibrillation, has been investigated. For example, the article "Prevention of Atrial Tachyarrhythmias Related to Advanced Interatrial Block by Permanent Atrial Resynchronization", by Daubert et al, Pace, Vol. 14, P. 648, 1991, discloses the use of synchronized pacing pulses delivered to the right and left atria to prevent onset of atrial tachyarrhythmias.

Recently, the theoretical possibility of employing pacing level pulses (e.g. less than 0.05 joules) to terminate fibrillation has been explored. For example, in the recent article "Regional Control of Atrial Fibrillation by Rapid Pacing in Conscious Dogs", by Allessie et al, published in Circulation, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site has been demonstrated. However, the depolarization wavefront created by such pulses does not propagate through the entire chamber, due to the varying polarization states of the tissue surrounding the stimulation site.

SUMMARY OF THE INVENTION

The present invention is directed toward providing a method and apparatus for terminating fibrillation of a chamber of the heart using stimulus pulses having energy levels in the range of those normally associated with cardiac pacing. In this manner, the pain associated with high energy shocks is eliminated. The primary application of the present application is believed to be termination of atrial fibrillation, however, termination of ventricular fibrillation may also be possible using the present invention. In the context of terminating atrial fibrillation, eliminating the delivery of high energy shocks avoids the possibility that such shocks could trigger ventricular tachycardia or fibrillation, which has been a substantial concern with respect to atrial defibrillators as described in the prior art.

The present invention pursues these objectives by providing simultaneously delivered pacing pulses at multiple sites distributed over a substantial portion of the heart chamber or chambers to be treated. It is envisioned that in most patients, the present invention will be practiced in conjunction with electrodes dispersed or extending over a substantial portion of the tissue of both atria. However, in some cases, electrodes may be applied only to one atrium, especially if the tissue responsible for initiating and/or maintaining fibrillation is localized in a single atrium.

Rather than attempt to synchronize the delivered pulses to atrial depolarizations sensed at a stimulation site, simultaneous pulse delivery at multiple dispersed sites in or on the chamber to be treated is intended to produce the result that capture of the atrial tissue will eventually occur at one or more stimulation sites at which the tissue is in an appropriate stage of the depolarization cycle, as per the Allessie article. Propagation of the depolarization wavefront locally in response to the delivered pacing pulse, toward tissue in the vicinity of stimulation sites closely adjacent the site at which capture initially occurs increases the probability that tissue adjacent an adjacent stimulation site will be in an appropriate stage of the depolarization-repolarization cycle to be captured by the next subsequent pacing pulse. As pacing pulses continue to be delivered, therefore, the amount of atrial tissue captured should gradually increase, with the end result of capturing a sufficient amount of atrial tissue to terminate fibrillation.

Polarity of the pacing pulses may be the same at all stimulation sites, or may vary. For example, pulses may be delivered between a remote electrode and all atrial electrodes, such that all stimulation sites on both atria may have the same polarity. Alternatively pacing pulses may be delivered between electrodes located on the atria such that all stimulation sites on the right atrium are at the same polarity and all stimulation sites on the left atrium are at the opposite polarity. As a further alternative, in cases wherein multiple, individual electrodes are distributed over the atria, polarity may alternate from electrode to electrode. Regardless of polarity, it is believed desirable to simultaneously deliver pulses to multiple adjacent stimulation sites distributed over the majority of the accessible tissue of each atrial chamber to be treated.

Unlike single or multi-site anti-tachycardia pacing according to the prior art, the present invention does not depend upon synchronizing delivered pacing pulses to the detected heart rhythm. Unlike high voltage defibrillation, the therapy provided by the present invention is not based upon the premise that a single delivered pulse will result in simultaneous depolarization of the fibrillating chamber, and does not raise a corresponding risk of induction of ventricular tachyarrhythmia.

Provision of multiple adjacent stimulation sites in accordance with the present invention may be accomplished by means of multiple, separate electrode surfaces distributed over or within the chamber to be treated. However, this result may be more easily accomplished by means of a smaller number (e.g. 2) large surface area electrodes, each covering or contacting a substantial portion of one or both atria. As discussed in U.S. Pat. No. 5,243,978, issued to Duffin, and incorporated herein by reference in its entirety, provision of pacing pulses to large surface electrodes appears to result in multiple sites of tissue stimulation, distributed over the tissue adjacent the electrode surfaces.

In commercial implementations of the invention, these large surface area electrodes may also function as defibrillation electrodes, and the invention may be embodied as part of an implantable pacemaker/cardioverter/defibrillator system. In this case, the large surface area electrodes may correspondingly also be employed for cardioversion or defibrillation in the event pacing therapies fail to terminate the detected arrhythmia. Alternatively, the invention may be embodied as a pacemaker only, and the electrodes in such case would be employed only for delivery of pacing level pulses. In either embodiment, the large surface area electrodes may also be employed to provide anti-tachycardia pacing as in the Duffin patent and/or to prevent the occurrence of atrial fibrillation as described in the above-cited article by Daubert et al.

DETAILED DESCRIPTION OF THE PREFERRED EMBODIMENT

Figure 1:
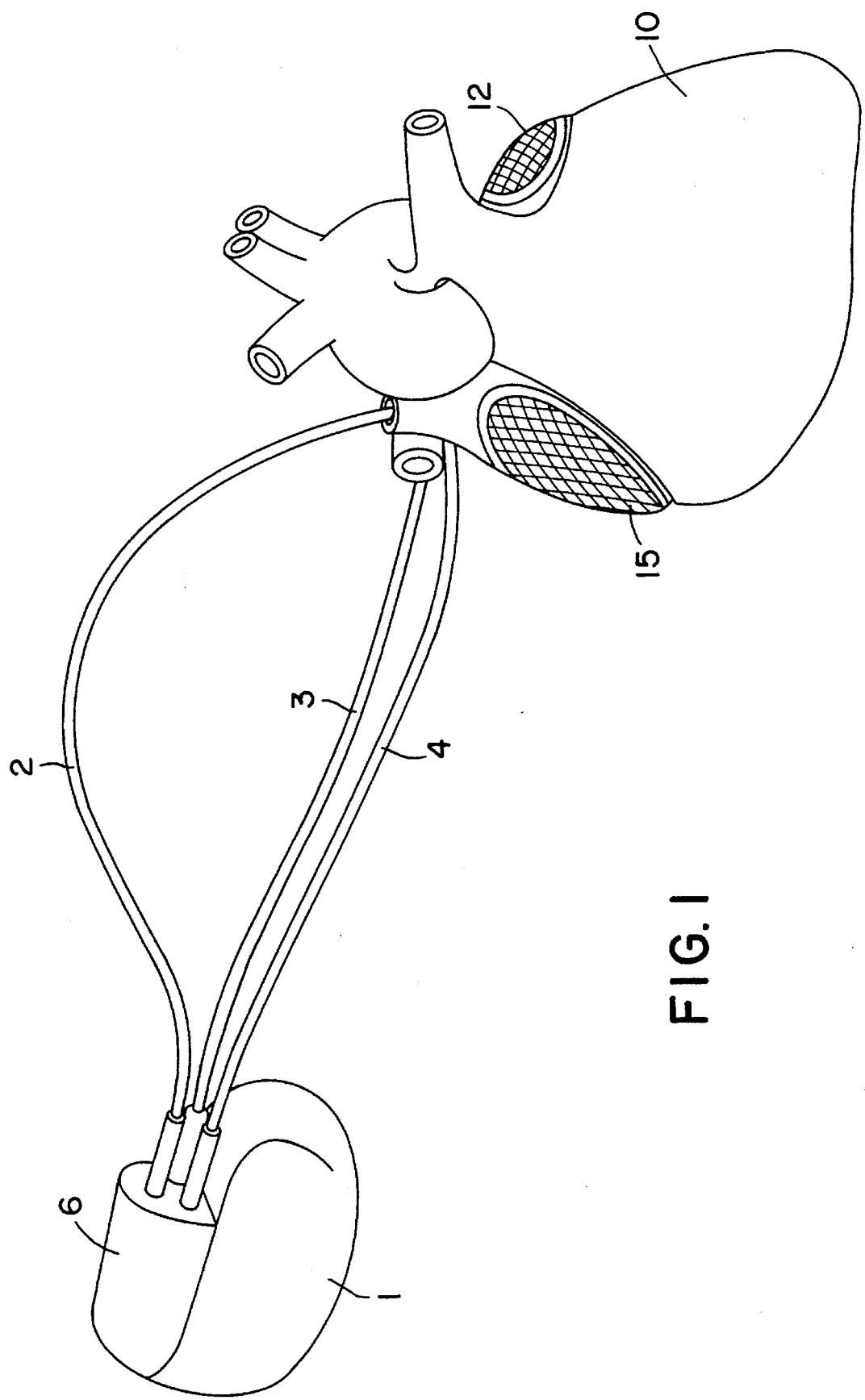
FIG. 1 is a plan view of an implantable pacemaker and a first associated lead system of the type in which the present invention may be embodied, illustrating the location of the leads and electrodes in relation to a human heart.
Figure 2:
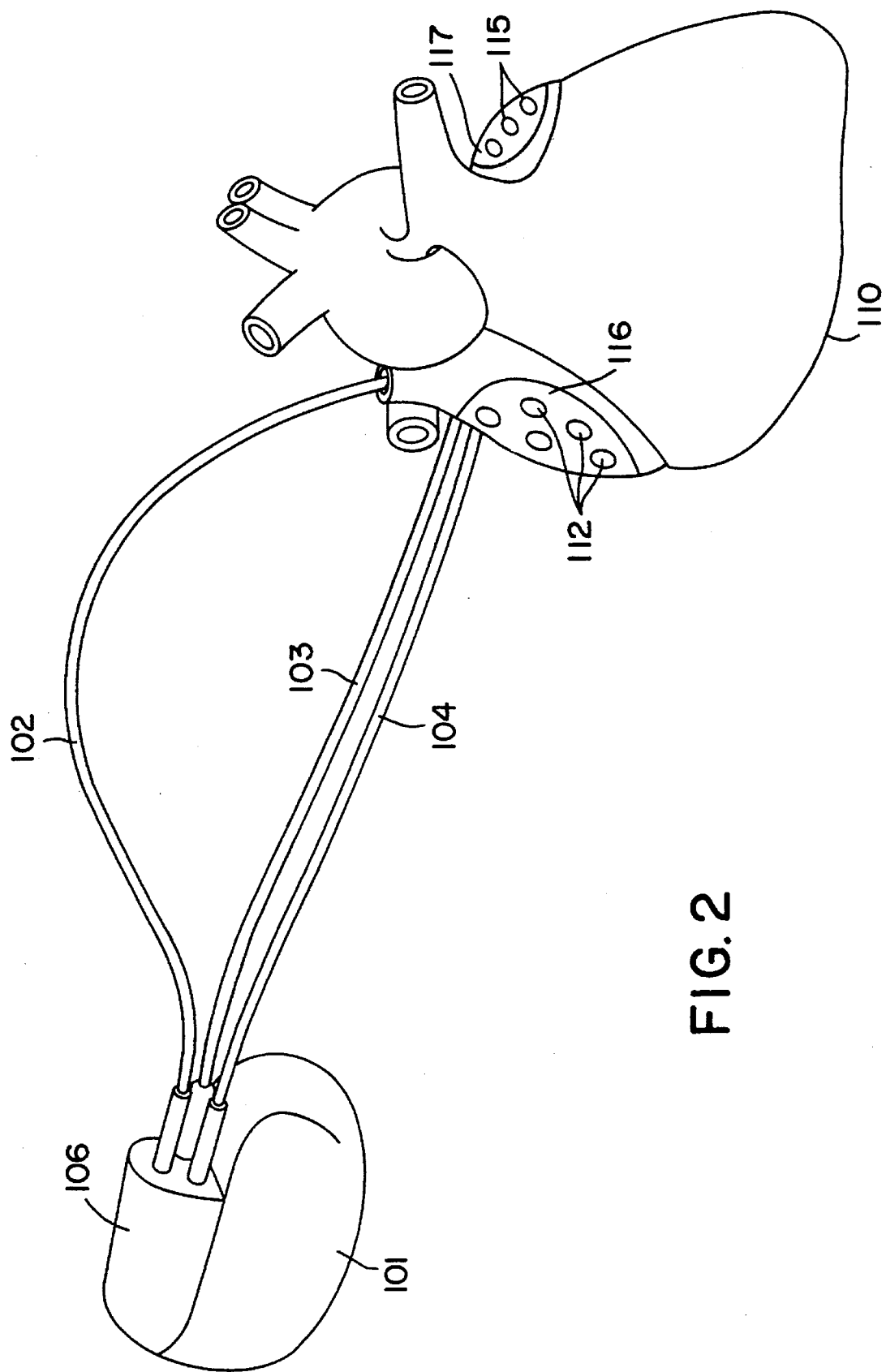
FIG. 2 is a plan view of an implantable pacemaker and a second associated lead system of the type in which the present invention may be embodied, illustrating the location of the leads and electrodes in relation to a human heart.

FIG. 1 is a plan view of an implantable pacemaker 1 and its associated lead system, in conjunction with a human heart 10. As illustrated, the device includes a right atrial lead 2, and two epicardial electrode leads 3, and 4. Leads 3 and 4 are provided with large surface area electrodes 12 and 15, respectively, adapted to located on the heart. The illustrated electrode system is adapted from the disclosure of U.S. Pat. No. 4,821,723 issued to Baker, et al, reduced in size to allow location on the right and left atria. However, it is believed that any pair of large surface area defibrillation electrodes appropriately sized for location in contact with on the atria, preferably extending over a majority of the accessible atrial tissue, may be usefully employed to practice the present invention. For example, electrodes as disclosed in U.S. Pat. No. 4,971,070 issued to Holleman, et al., incorporated herein by reference in its entirety, may also be used. Electrodes of this type have in fact been tested at the request of the inventor of the present application and it has been determined that, in conjunction with a cardiac pacemaker output stage modified to pace into a 50 ohm load, reliable cardiac pacing may be accomplished with an output of 5 volts. In any case, it is desired that the epicardial electrodes have a relatively large surface area, and be disbursed over a substantial portion of the atrial epicardium of the heart. Alternatively, multiple electrode leads connected in common may be substituted for individual large surface area electrodes, if desired, as illustrated in FIG. 2. Similar considerations would apply if the ventricles were to be treated.

The right atrial lead 2 may be a conventional bipolar pacing lead, serving to perform normal cardiac pacing functions and to sense atrial depolarizations. Alternatively, lead 2 may be a unipolar lead, and cardiac pacing and/or sensing of ventricular depolarizations may be accomplished between an electrode located on lead 2 and a patch electrode located on the epicardium or an electrode located on the housing of the device 1.

For purposes of the present invention, it is envisioned that the electrodes located on the right atrial lead 2, or a corresponding epicardial electrode or electrodes will be used for routine AAI pacing in the presence of bradycardia, or for sensor based rate responsive AAIR mode cardiac pacing, if the device is so equipped, and for anti-tachycardia pacing, if the physician so desires. However, in response to detection of atrial fibrillation, an extended series of pacing level pulses are delivered using the large surface area electrodes 12 and 15.

Based upon work done in conjunction with the above-cited Duffin Patent, it appears that pacing pulses delivered through large surface areas stimulate depolarization of tissue at multiple sites around the chamber paced. It is known from the above-cited article by Allessie that pacing level pulses, if timed appropriately, can be effective to locally to depolarize atrial tissue during atrial defibrillation. The provision of multiple effective stimulation sites, in conjunction with an extended series of pacing pulses thus increases the likelihood that at one stimulation site, a pulse will be delivered at an appropriate time during the depolarization/repolarization cycle. At such a site, a local depolarization wavefront will be initiated, tending to synchronize the tissue adjacent the site. On the next sequential pulse, therefore, a greater area of atrial tissue will likely be in an appropriate portion of the depolarization/repolarization cycle, allowing for stimulation sites adjacent the original stimulation site to effectively trigger local, synchronized depolarization wavefronts. Over an extended series of pulses, therefore, greater amounts of atrial tissue may be brought into synchrony, and the level of synchrony provided by the multiple stimulation sites, in conjunction with the rapid rate of delivered pulses are intended to prevent depolarization wavefronts originating in adjacent fibrillating tissue from interfering with the synchronized tissue's paced depolarization cycle. As the series of pulses continues, a sufficient percentage of the atrial tissue may be captured to terminate the fibrillation.

It is not envisioned that the pacing level therapy provided as discussed above will be successful to terminate all atrial fibrillation episodes in any single patient. Repeated termination attempts, however, can be undertaken without severe consequences. Unlike ventricular fibrillation, atrial fibrillation is not an immediately life threatening condition. If the invention is embodied in a device which also includes high voltage atrial defibrillation capabilities, the pacing level therapy of the present invention may be employed as an initial therapy for atrial fibrillation, with the intended goal of simply reducing the number of high voltage shocks given.

The pacemaker may deliver an extended series of pacing pulses (e.g. 20–100) and thereafter monitor the atrial electrogram to determine whether the pacing level pulses were effective in terminating the sensed fibrillation. Alternatively or in addition, the pacemaker may monitor the atrial electrogram to determine whether fibrillatory activity has ceased during delivery of the pulse train and terminate the delivery of the pulse train in response. Because atrial defibrillation is not dangerous acutely, it is not necessary that the first attempt to terminate be successful, and multiple attempts may be made, with pulse interval, amplitude or number varied between attempts, much as successive anti-tachycardia pacing regimens are applied to the ventricle by implantable pacemaker/cardioverter/defibrillators presently available.

FIG. 2 is a plan view of an implantable pacemaker 101, corresponding to pacer 1 as discussed above in conjunction with FIG. 1, and an associated alternative lead system, in conjunction with a human heart 110. As illustrated, the device includes a right atrial lead 102, corresponding to lead 2, illustrated in FIG. 1, and two epicardial electrode leads 103, and 104. Leads 103 and 104 are provided with multiple electrodes 112 and 115, respectively, located on a flexible base pads 116 and 117, adapted to be located on the right and left atria of the heart.

Figure 3:
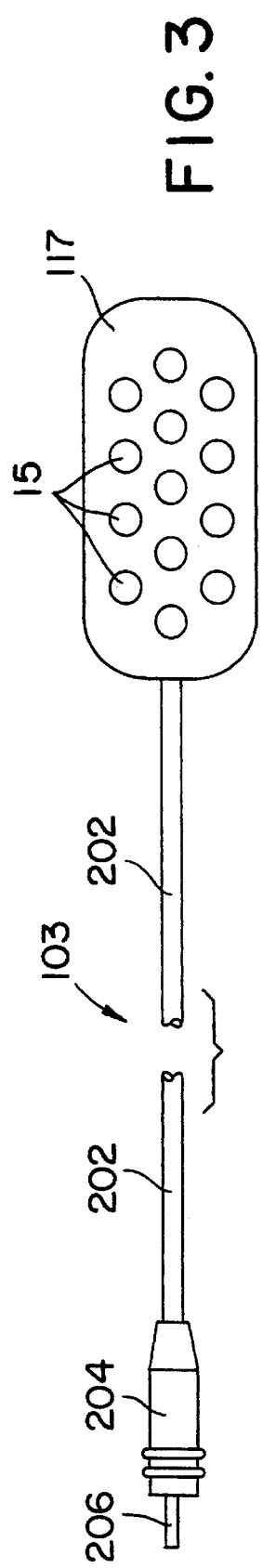
FIG. 3 is a plan view of an first embodiment of an atrial epicardial electrode lead for providing multiple stimulation sites.

FIG. 3 is a plan view of lead 103, as illustrated in FIG. 2. The lead includes multiple electrodes 115, located on silicone rubber electrode pad 117, all coupled in common to a single connector pin 206, mounted to connector assembly 204. Extending between connector assembly 204 and electrode pad 117 is an elongated insulated conductor 202, coupling pin 206 to electrodes 115. Alternatively, each of electrodes 115 may be provided with its own mutually insulative conductor, coupled to a multi-contact connector system, located at the proximal end of the lead, with inter-connection of the electrodes controlled internally to the associated pulse generator. As a further alternative, individual electrodes might be distributed over the interior of the atria, using deployable electrode arrays similar to that disclosed in U.S. Pat. No. 5,239,999, issued to Imran, incorporated herein by reference in its entirety.

Figure 4:
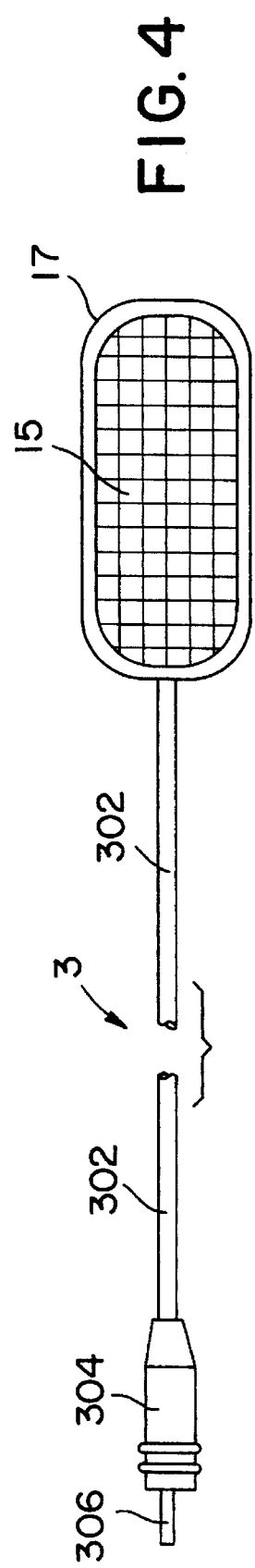
FIG. 4 is a plan view of an first embodiment of an atrial epicardial electrode lead for providing multiple stimulation sites.

FIG. 4 is a plan view of lead 3, illustrated in FIG. 1. A large surface area mesh electrode 15 is provided, mounted to a silicone rubber electrode head 17. A connector assembly 304 is provided at the proximal end of the lead, carrying a connector pin 306. Electrode 15 is coupled to connector pin 306 by means of an elongated insulated conductor 302.

Figure 5:
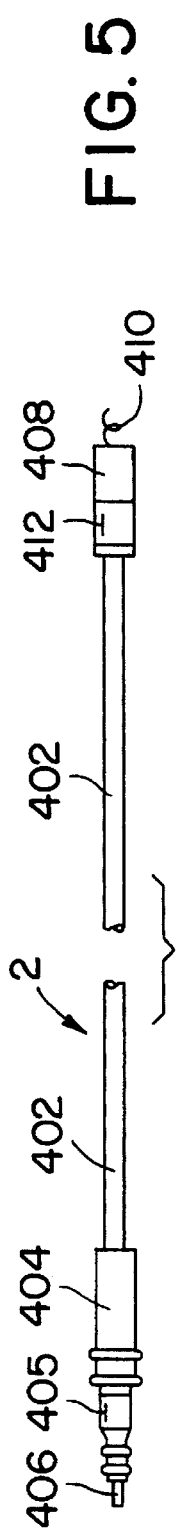
FIG. 5 is a plan view of a transvenous bipolar lead which may be employed for atrial or ventricular sensing and pacing; in addition to the leads illustrated in FIGS. 3 and 4.

FIG. 5 is a plan view of lead 2, illustrated in FIG. 1. At the distal end of lead 2 is an electrode head assembly 408, which carries an advanceable helical electrode 410 and a ring electrode 412. At the proximal end of the lead is located an electrode connector assembly 404, which carries a connector 405 and a connector pin 406. Connector pin 406 is coupled to advanceable helix 410 by means of a rotatable insulated conductor located within the lead body 402. Rotation of connector pin 406 causes helical electrode 410 to screw out of the distal end of the electrode 408 and into heart tissue. Connector ring 405 is coupled to ring electrode 412 by means of a second insulated conductor, located within lead body 402. As illustrated, lead 2 corresponds to commercially marketed Model 6957 bipolar screw-in leads sold by Medtronic, Inc. However, other bipolar and/or unipolar leads may be substituted for lead 2, depending upon the preference of the physician.

Figure 6:
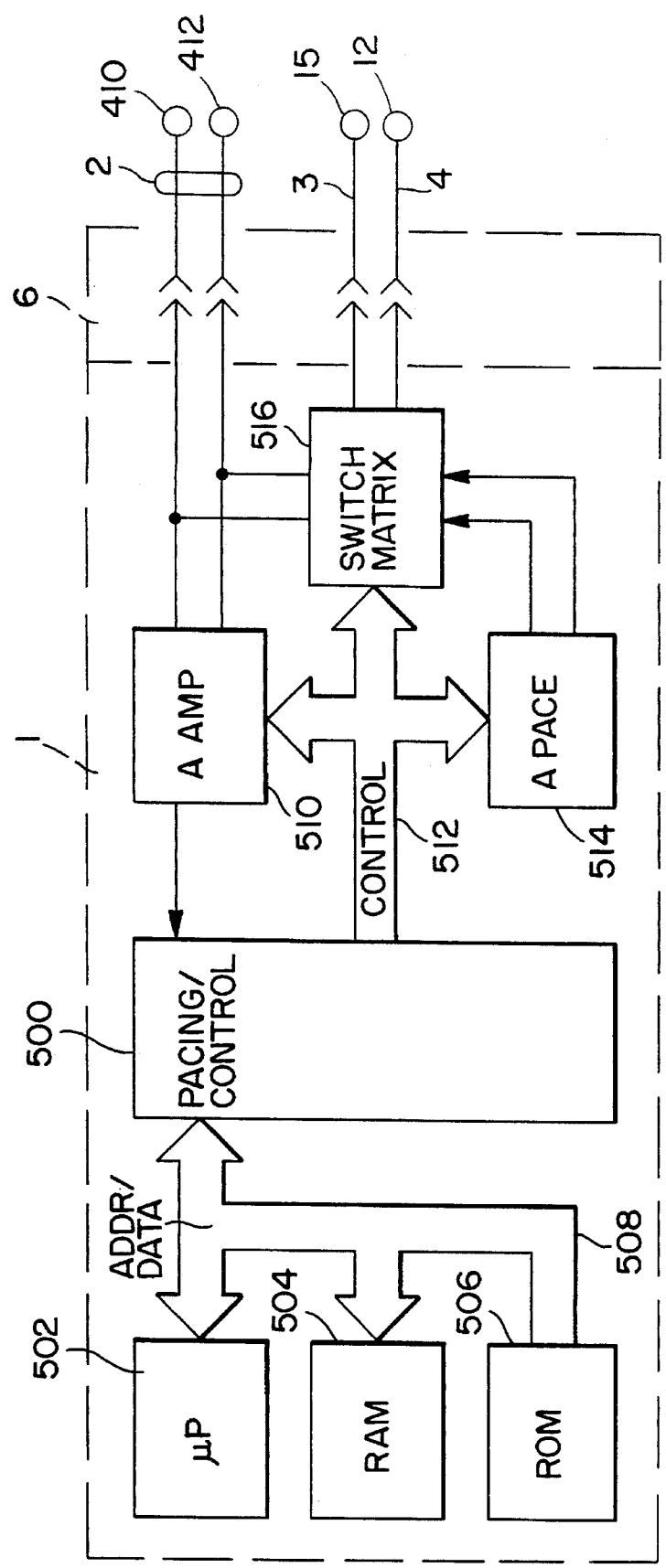
FIG. 6 is block diagram of a prior art implantable pacemaker, to which a low impedance pacing output stage and an associated switch matrix, allowing selective delivery of pacing pulses to the electrodes of FIGS. 3 or 4 has been added.

FIG. 6 is a block diagram illustrating the major functional components of the implanted pacemaker 1, illustrated in FIG. 1. Timing and control functions are preferably accomplished using a microprocessor based system, corresponding to those used in presently available pacemakers. The basic function and operation of the timing and control logic 500, microprocessor 502, random access memory 504 and read only memory 506 may correspond to corresponding elements in the microprocessor controlled systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties.

Timing/control circuitry 500, in conjunction with microprocessor 502 detects the occurrence of bradycardia and/or tachycardia and in response thereto controls the delivery of the various pacing therapies available via control bus 512. Microprocessor 502 also detects the occurrence of atrial fibrillation based on sensed atrial depolarizations. Detection of atrial fibrillation may be accomplished by microprocessor 502 using any of the various detection methodologies known to the art. Generally, atrial fibrillation may be detected in response to an extended series of high rate (e.g. greater than 240 b.p.m.) atrial depolarizations. If greater specificity for atrial fibrillation is desired, analysis of regularity of rate waveform morphology may also be employed. Termination of atrial fibrillation may be detected in response to a decrease in the rate of atrial depolarizations and/or an increase in their regularity. Appropriate detection methodologies are disclosed in the above-cited PCT application by Adams et al, and in the article "Automatic Tachycardia Recognition", by Arzbaecher et al, published in Pace, Vol. 7, May–June 1984, part II, pages 541–547, both incorporated herein by reference in their entireties.

The operation of microprocessor 502 is controlled by programming stored in read only memory 506 and in random access memory 504. The operation of the device may be altered by the physician by altering the programming stored in memory 504, using control and telemetry circuitry conventional in implantable stimulators. Memory 504 may also be employed for storing measured parameters, such as R-R intervals, P-P intervals, P-R intervals and P or R-wave widths and amplitudes. Memory 504 may also be employed to store digitized electrocardiograms sensed using the various electrodes provided. Communication to and from the microprocessor 502, memories 504 and 506 and control logic 500 is accomplished using address/data bus 508.

For purposes of applying the pacing level anti-fibrillation therapy of the present invention, pacing pulse rates of several hundred beats per minute are preferably available. The specific rate may be selected by the implanting physician, following measurement of the rate of the patient's fibrillation. Alternatively, the device may employ stored P-P intervals to specify a pacing rate in excess of the atrial fibrillation rate. The pacing rate may be, for example, slightly greater than the rate of the detected fibrillation, as in the Alessie et al article. The intervals separating pulses in a pulse train may be constant, with intervals being varied from one pulse train to the next in response to failure of a pulse train to terminate atrial fibrillation. As the delivered pulses are not specifically intended to be delivered synchronized to the atrial tissue adjacent the sensing electrodes, synchronization of the pacing pulse train to sensed atrial depolarizations is not necessary, and the pulse train can be initiated at any convenient time following detection of atrial fibrillation.

As a practical matter, because various portions of the atria will be in different stages of the depolarization-repolarization cycle, even if the first pulse in a pulse train is delivered synchronized to an atrial depolarization sensed at one location, the delivered pulses will be asynchronous to depolarizations of other portions of the atria. For example, if large surface area electrodes are located one on each atrium, with sensing electrodes located in the right atrium, the delivered pacing pulse train will be generally asynchronous to depolarizations of the left atrium, regardless of the relationship of the pacing pulses to the sensed right atrial electrogram.

Atrial sensing circuit 510 can be any conventional cardiac sense amplifier circuits equivalent to any prior art atrial cardiac sensing circuits employed in previous devices. For example, the sensing circuit may correspond to the circuit disclosed in U.S. Pat. No. 4,266,551 issued to Stein on May 21, 1981, U.S. Pat. No. 4,275,737 issued to Thompson et al, U.S. Pat. No. 4,649,931 issued to Beck on Mar. 17, 1987, all of which are incorporated herein by reference in their entireties.

The low impedance pacing output circuitry 710 may correspond generally to the output circuitry illustrated in U.S. Pat. No. 4,406,286 issued to Stein on Sep. 27, 1983 or U.S. Pat. No. 4,340,062 issued to Thompson et al. on Jul. 20, 1982, both of which are also incorporated herein by reference in their entireties, with the exception that the circuit must be slightly modified to pace at higher voltages, (e,g. up to 10 or 15 volts) into somewhat lower impedances than typical implantable pacers, e.g., 50 ohms or less. This result may be accomplished by using a larger value output capacitor, for example in the range of 100 μF, and by increasing the voltage and current available for recharging the larger output capacitor. These modifications are believed to be well within the ability of one skilled in the art, and are therefore not discussed in detail. For purposes of the present invention any circuit capable of generating pacing pulses at an amplitude of 5 to 15 volts, with a pulse width of about 0.1 millisecond to about 5 milliseconds, should be sufficient. Other low energy pulses (i.e. 0.05 joules or less) having parameters outside these values may also be employed.

Atrial sense amp circuitry 510 is coupled to right atrial lead 2, and to a pair of electrodes 408 and 410, located adjacent to distal end of the lead. Alternatively, sense amp circuit 510 may be coupled to only one of the electrodes 408 and 410, and may sense between that electrode and the conductive housing of the implantable device or one of the large surface electrodes.

Atrial anti-tachycardia and anti-bradycardia pacing therapies delivered by the device may include those described in U.S. Pat. No. 4,880,005, issued to Pless, also incorporated herein by reference in its entirety. A device generally as disclosed in the Pless et al patent may serve as the starting point for practicing the invention, with software in ROM 506 for controlling atrial fibrillation detection and multi-site pulse delivery added along with low impedance pacing circuit 520 and switch matrix 516. If programmed by the physician to do so, the device according to the present invention is capable of selectively coupling the low impedance pacing output stage 514 to large surface area defibrillation electrodes 12 and 15, and of delivering trains of pacing level pulses thereto, under control of the timing/control circuitry 500.

Switch matrix 516 shown in block format is simply a collection of one or more FET and/or SCR switches activated under control of timing/control circuitry 500 to selectively pacing circuitry 516 to small surface area electrodes 408 and 410 or to large surface electrodes 12 and 15. Thus, atrial anti-tachycardia and anti-bradycardia pacing may also be performed using either the large surface area defibrillation electrodes or using conventional pacing electrodes.

Figure 7:
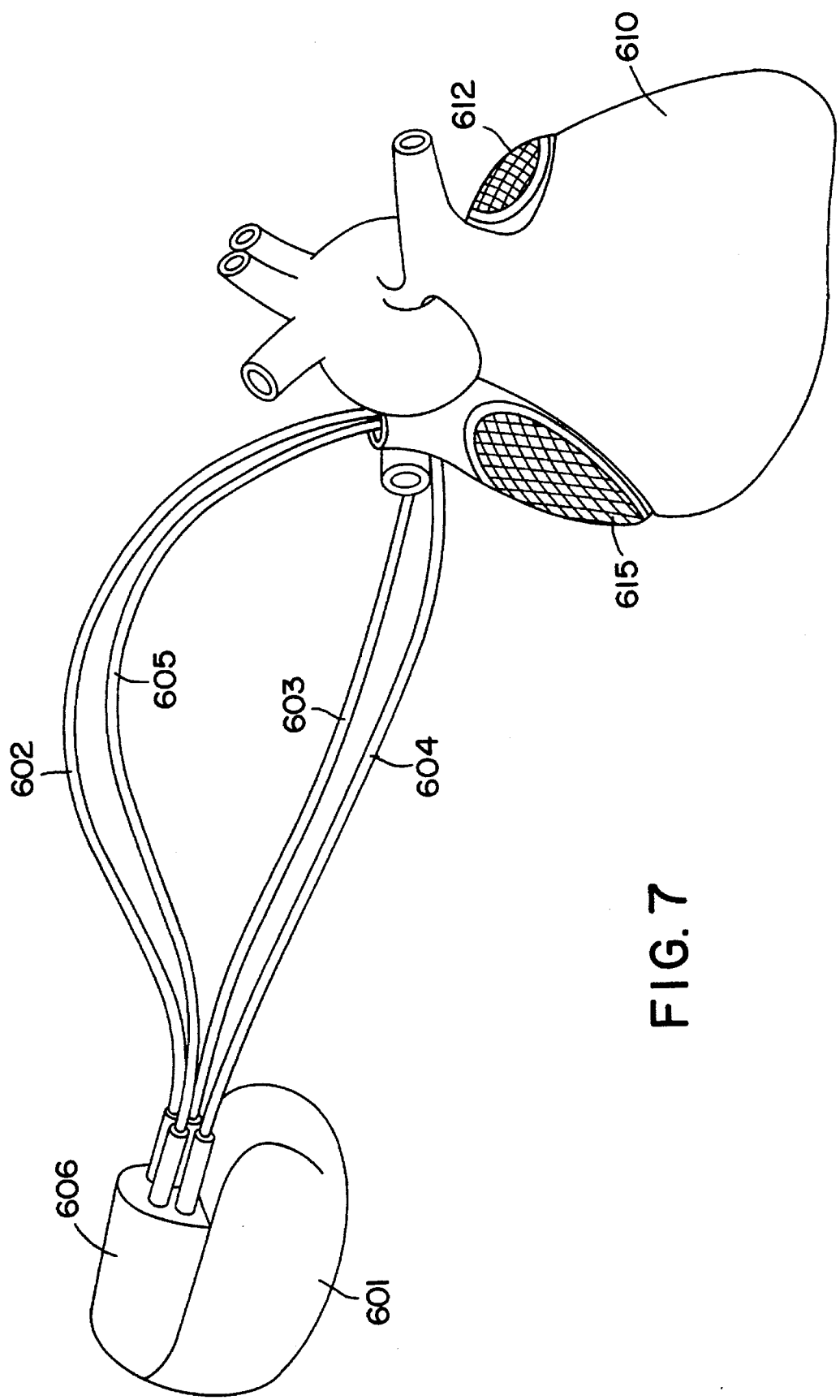
FIG. 7 is a plan view of an implantable pacemaker/cardioverter/defibrillator and a third associated lead system of the type in which the present invention may be embodied, illustrating the location of the leads and electrodes in relation to a human heart.

FIG. 7 is an illustration of a pacemaker/cardioverter/defibrillator 601 and an associated lead system, in conjunction with a human heart 610. As illustrated, the device includes a right atrial lead 602, a right ventricular lead 605 and two epicardial electrode leads, 603 and 604. Leads 603 and 604 correspond to lead 3 and 4 illustrated in FIG. 1. Leads 602 ad 605 both correspond to lead 2 illustrated in FIG. 1, and illustrated in more detail in FIG. 5. The electrode pair located at the distal end of lead 602 is located in the right atrium. The electrode pair located at the distal end of electrode lead 605 is located in the right ventricle. For purposes of the present invention, it is envisioned that electrodes located on lead 605 will be employed for ventricular bradycardia pacing and sensing and that the electrodes located on lead 602 will be employed for atrial pacing and sensing functions. The device may operate to provide DDD mode pacing employing pacing of both the atrial and ventricular chambers, or to simply provide ventricular bradycardia pacing. Similarly, the electrodes located on lead 602 may be employed to provide anti-tachycardia pacing in the atrium, if desired.

In response to detection of atrial fibrillation, the device functions as discussed in conjunction with the pacemaker illustrated in FIG. 1. An extended series of pacing level pulses is delivered using the large surface area electrodes 612 and 615, in the same fashion as described in conjunction with the pacemaker described in FIG. 1. Electrodes 612 and 616 may also optionally be employed to deliver anti-tachycardia pacing pulses.

Figure 8:
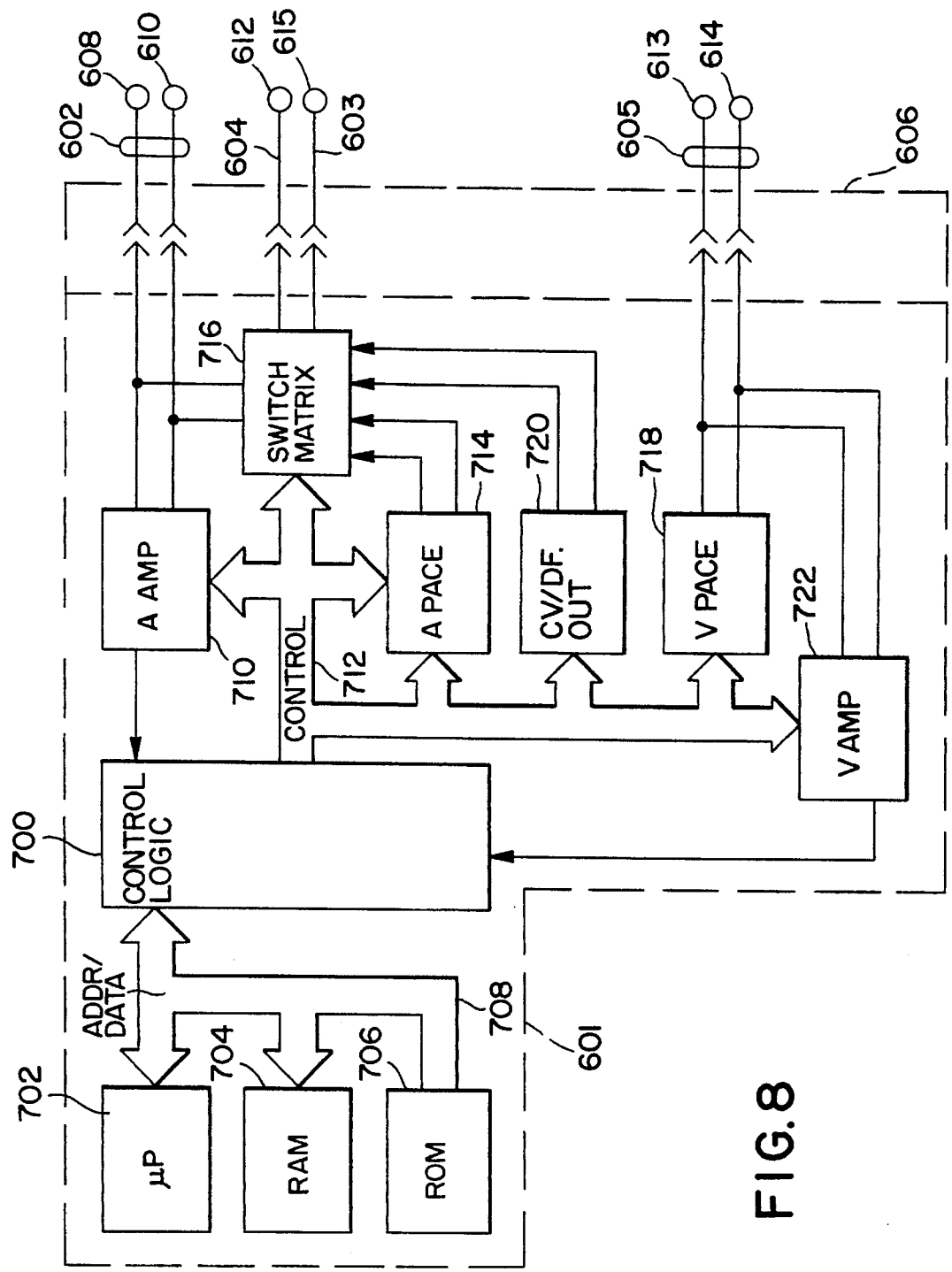
FIG. 8 is block diagram of a prior art implantable pacemaker/cardioverter/defibrillator, to which a low impedance pacing output stage and an associated switch matrix, allowing selective delivery of anti-bradycardia pacing pulses and anti-tachycardia pacing pulses to the cardioversion/defibrillation electrodes has been added.

FIG. 8 is a block diagram illustrating the major functional components of the implanted pacemaker/cardioverter/defibrillator 601 illustrated in FIG. 7. Timing and control functions are preferably accomplished using a microprocessor based system, corresponding to those used in presently available pacemaker/cardioverter/defibrillator systems. The basic function and operation of the timing and control logic 700, microprocessor 702, random access memory 704 and read only memory 706 may correspond to corresponding elements in the microprocessor controlled systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties. Timing/control circuitry 700, in conjunction with microprocessor 702 detects the occurrence of bradycardia and/or tachycardia and in response thereto controls the delivery of the various pacing, cardioversion and defibrillation therapies available via control bus 712. The operation of microprocessor 702 is controlled by programming stored in read only memory 706 and in random access memory 704. The operation of the device may be altered by the physician by altering the programming stored in memory 704, using control and telemetry circuitry conventional in implantable stimulators. Memory 704 may also be employed for storing measured parameters, such as R-R intervals, P-P intervals, P-R intervals and P or R-wave widths and amplitudes. Memory 704 may also be employed to store digitized electrocardiograms sensed using the various electrodes provided. Communication to and from the microprocessor 702, memories 704 and 706 and control logic 70.0 is accomplished using address/data bus 708.

In the context of the present invention, it is envisioned that the high voltage cardioversion and defibrillation therapies provided may simply correspond to those available in the prior art. High voltage atrial defibrillation/cardioversion pulses are provided by the Defib/CV output circuit 720, under control of timing/control circuitry 700. Typically, this circuit will be capable of charging and discharging high voltage capacitors therein to produce output pulses in excess of 300 volts into a 50 ohm load. In any case, the circuit 722 should be capable of delivering pulses well in excess of 0.2 joules. Examples of appropriate circuitry for accomplishing the generation of cardioversion and defibrillation pulses are set forth in U.S. Pat. No. 4,595,009 issued to Leinders on Jun. 17, 1986, U.S. Pat. No. 4,548,209 issued to Wielders on Oct. 22, 1985, U.S. Pat. No. 4,693,253 issued to Adams on Sep. 15, 1987, U.S. Pat. No. 4,953,551 issued to Mehra et al. on Sep. 4, 1990, or U.S. Pat. No. 5,163,427 issued to Keimel, all of which are also incorporated herein by reference in their entireties. For purposes of the present invention, it is believed that any prior art defibrillation/cardioversion output circuit may be usefully employed.

Atrial and ventricular sensing circuits 710 and 722 may be conventional cardiac sense amplifier circuits equivalent to any prior art cardiac sensing circuits employed in previous devices, as discussed above in conjunction with amplifier 510, FIG. 6. Low impedance pacing output circuitry 714 similarly corresponds to output circuit 514, FIG. 6.

Ventricular sense amp circuitry 722 is coupled to right ventricular lead 605, and to a pair of electrodes 614 and 616, located adjacent to distal end of the lead. Alternatively, sense amp circuit 722 may be coupled to only one of the electrodes 614 and 616, and may sense between that electrode and the conductive housing of the implantable device or one of the large surface electrodes.

Similarly, atrial sense amp circuitry 710 is coupled to right atrial lead 602, and to a pair of electrodes 608 and 610, located adjacent to distal end of the lead. Alternatively, sense amp circuit 710 may be coupled to only one of the electrodes 608 and 610, and may sense between that electrode and the conductive housing of the implantable device or one of the large surface electrodes.

Ventricular bradycardia pacing and atrial cardioversion, and defibrillation therapies may correspond to any prior art implantable pacemaker/cardioverter/defibrillator, in particular, a device as disclosed in the above-cited PCT Patent Application by Adams et al may serve as the starting point for practicing the invention, with low impedance pacing circuit 720 and switch matrix 716 added. If programmed by the physician to do so, the device according to the present invention is capable of selectively coupling the low impedance pacing output stage 714 to the large surface area defibrillation electrodes 612 and 615, and delivering trains of pacing level pulses thereto, under control of the timing/control circuitry 700. Switch matrix 7 16 shown in block format is simply a collection of one or more FET and/or SCR switches activated under control of timing/control circuitry 700 to selectively couple either the defibrillation/cardioversion output circuitry 720 or the low impedance pacing output circuitry 714 to the large surface area electrodes 612 and 615. Examples of switch matrixes of controlled electrical switches used to selectively couple defibrillation electrodes to output circuitry may be found in the above-cited Mehra et al. patent, the above-cited Keimel et al. Patent or U.S. Pat. No. 4,800,883 issued to Winstrom on Jan. 31, 1989, incorporated herein by reference in its entirety. It is believed that any of these systems may be adapted for switching the connection of electrodes 612 and 615 between the high voltage output circuitry 720 and the low impedance pacing output circuitry 714. It is also believed that construction of such switch matrixes is well within the ability of one of skill in the art, given the teaching in the cited references. Switch matrix 716 preferably also may selectively couple pacing circuitry 716 to small surface area electrodes 608 and 610. Thus, atrial anti-tachycardia and anti-bradycardia pacing may be performed using either the large surface area defibrillation electrodes or using conventional pacing electrodes.

While the large surface area electrode system employed by the present invention does require a pacing pulse generator with higher output current capabilities, the overall energy delivered with each such pacing pulse is not substantial as compared to the delivery of a cardioversion or defibrillation pulse. It is believed that in most cases, pacing pulses of 5 millijoules or less should be sufficient. In some cases, it is believed that pacing using large surface area epicardial electrodes can be accomplished readily using individual pulses having energy levels of less than 1 millijoule. For example, delivery of a 5 volt pacing pulse into a 50 ohm load, using a 0.5 millisecond pulse width (the parameters tested) results in the expenditure of only 0.25 millijoules per pulse. While this is somewhat of an increase over the energy level of standard pacing pulses, it should not pose a significant problem for occasionally activated pulse regimens. Further, while the electrode systems disclosed above employ epicardial electrodes for termination of fibrillation, transvenous leads might alternately be employed, located in the atria, coronary sinus, or other vessels adjacent the atria to provide electrode surfaces dispersed in or around substantial portions of the atria.

While the embodiments disclosed above employ the sensed electrogram of the heart to detect fibrillation, other defibrillation detection methods can be employed as well, given that synchronization to the sensed depolarizations is not desired. For example, a pressure transducer could be employed to detect the cessation of mechanical pumping activity of the heart, in the manner disclosed in U.S. Pat. No. Re 27,757, issued to Mirowski et. al. on Sep. 11, 1973, incorporated herein in its entirety. Any method of detection of fibrillation is believed workable in the context of the present invention.

In conjunction with the above disclosure, I claim:

1. An anti-fibrillation pacemaker, comprising:

means for detecting the presence of fibrillation in said chamber;

electrode means for simultaneously delivering pacing pulses to multiple sites dispersed over a chamber of a patient's heart; and pulse generator means responsive to the detection of fibrillation for providing a series of cardiac pacing pulses to said electrode means to simultaneously stimulate said multiple sites until fibrillation is terminated.

2. A pacemaker according to claim 1 wherein said pulse generator means comprises means for providing said pacing pulses unsynchronized to depolarizations of said chamber.

3. A pacemaker according to claim 1 wherein said electrode means comprises an epicardial electrode lead.

4. A pacemaker according to claim 1 or claim 2 wherein said pulse generator means comprises means for generating pulses of 0.05 joules or less for application to said chamber.

5. A pacemaker according to claim 1 or claim 2 wherein said pulse generator means comprises means for generating pulses of 5 millijoules or less for application to said chamber.

6. A method of treating fibrillation, comprising:

mounting an electrode on or in a chamber of a patient's heart, such that said electrode is located adjacent multiple sites dispersed over said chamber;

detecting the presence of fibrillation;

response to the detection of fibrillation, providing a series of cardiac pacing pulses to said electrode to simultaneously stimulate said multiple sites, unsynchronized to depolarizations of said chamber, to terminate fibrillation.

7. A method according to claim 6 wherein said mounting step comprises mounting an epicardial electrode lead having a single electrode surface extending over said chamber.

8. A method according to claim 6 wherein said mounting step comprises mounting an epicardial electrode lead having multiple electrode surfaces dispersed over said chamber.

9. A method according to claim 6 or claim 7 or claim 8 wherein said step of providing pacing pulses comprises generating pulses of 0.05 joules or less for application to said chamber.

10. A method according to claim 6 or claim 7 or claim 8 wherein said step of providing pacing pulses comprises generating pulses of 5 millijoules or less for application to said chamber.

11. A method according to claim 6 or claim 7 or claim 8 wherein said mounting step comprises mounting said electrode to an atrium of said patient's heart.

12. A method of treating fibrillation, comprising:

mounting an electrode lead having an electrode on or in a chamber of a patient's heart, such that said electrode is located adjacent multiple sites dispersed over said chamber;

detecting the presence of fibrillation;

responsive to the detection of fibrillation, providing a series of cardiac pacing pulses to said electrode to simultaneously stimulate said multiple sites to terminate fibrillation.

13. A method according to claim 12 wherein said mounting step comprises mounting an epicardial electrode lead having a single electrode extending over said chamber.

14. A method according to claim 12 wherein said mounting step comprises mounting an epicardial electrode lead having multiple electrodes dispersed over said chamber.

15. A method according to claim 12 wherein said step of providing pacing pulses comprises generating pulses of 0.05 joules or less for application to said chamber.

16. A method according to claim 12 wherein said step of providing pacing pulses comprises generating pulses of 5 millijoules or less for application to said chamber.

17. A method according to claim 12 wherein said mounting step comprises mounting said electrode to an atrium of said patient's heart.

* * * * *